(12) United States Patent
Watanabe et al.

(10) Patent No.: US 11,487,027 B2
(45) Date of Patent: Nov. 1, 2022

(54) RADIATION IMAGING APPARATUS AND RADIATION IMAGING SYSTEM

(71) Applicant: CANON KABUSHIKI KAISHA, Tokyo (JP)

(72) Inventors: Minoru Watanabe, Yokohama (JP); Kentaro Fujiyoshi, Tokyo (JP); Ryosuke Miura, Ichikawa (JP)

(73) Assignee: CANON KABUSHIKI KAISHA, Tokyo (JP)

(*) Notice: Subject to any disclaimer, the term of this patent is extended or adjusted under 35 U.S.C. 154(b) by 111 days.

(21) Appl. No.: 16/929,699

(22) Filed: Jul. 15, 2020

(65) Prior Publication Data
US 2020/0348424 A1    Nov. 5, 2020

Related U.S. Application Data

(63) Continuation of application No. PCT/JP2018/043952, filed on Nov. 29, 2018.

(30) Foreign Application Priority Data

Feb. 21, 2018    (JP) .............................. JP2018-029053

(51) Int. Cl.
*G01T 1/20*    (2006.01)
*G01T 1/17*    (2006.01)

(52) U.S. Cl.
CPC ............ *G01T 1/20184* (2020.05); *G01T 1/17* (2013.01)

(58) Field of Classification Search
CPC .............................. G01T 1/20184; G01T 1/17
See application file for complete search history.

(56) References Cited

U.S. PATENT DOCUMENTS

| 7,205,547 | B2 | 4/2007 | Ishii et al. |
| 7,205,568 | B2 | 4/2007 | Watanabe et al. |
| 7,381,965 | B2 | 6/2008 | Ishii et al. |
| 7,435,968 | B2 | 10/2008 | Watanabe et al. |

(Continued)

FOREIGN PATENT DOCUMENTS

| JP | 2015-212645 | 11/2015 |
| JP | 2016-039463 | 3/2016 |

(Continued)

OTHER PUBLICATIONS

U.S. Appl. No. 16/989,118, Ryosuke Miura, filed Aug. 10, 2020.

*Primary Examiner* — David P Porta
*Assistant Examiner* — Jeremy S Valentiner
(74) *Attorney, Agent, or Firm* — Venable LLP

(57) ABSTRACT

An imaging region including a plurality of detection elements each including a conversion element configured to convert radiation into an electric signal, a first signal line, and a signal processing circuit configured to process a signal output via the first signal line, wherein the plurality of detection elements include a first detection element and a second detection element which are connected to the first signal line, a sensitivity of the first detection element to radiation is set to be different from a sensitivity of the second detection element to radiation, and the signal processing circuit generates information related to irradiation of radiation to the imaging region based on signals from the first detection element and the second detection element which are connected to the first signal line.

11 Claims, 9 Drawing Sheets

(56) References Cited

U.S. PATENT DOCUMENTS

| | | | |
|---|---|---|---|
| 7,465,933 B2 | 12/2008 | Ishii et al. | |
| 7,470,908 B2 | 12/2008 | Ishii et al. | |
| 7,488,948 B2 | 2/2009 | Ishii et al. | |
| 7,535,506 B2 | 5/2009 | Nomura et al. | |
| 7,541,617 B2 | 6/2009 | Mochizuki et al. | |
| 7,557,355 B2 | 7/2009 | Mochizuki et al. | |
| 7,629,564 B2 | 12/2009 | Mochizuki et al. | |
| 7,642,517 B2 | 1/2010 | Ishii et al. | |
| 7,645,976 B2 | 1/2010 | Watanabe et al. | |
| 7,750,422 B2 | 7/2010 | Watanabe et al. | |
| 7,812,313 B2 | 10/2010 | Mochizuki et al. | |
| 7,812,317 B2 | 10/2010 | Watanabe et al. | |
| 7,858,947 B2 | 12/2010 | Mochizuki et al. | |
| 7,897,930 B2 | 3/2011 | Mochizuki et al. | |
| 7,923,695 B2 | 4/2011 | Ishii et al. | |
| 7,932,946 B2 | 4/2011 | Ishii et al. | |
| 8,067,743 B2 | 11/2011 | Ishii et al. | |
| 8,084,745 B2 | 12/2011 | Mochizuki et al. | |
| 8,154,641 B2 | 4/2012 | Nomura et al. | |
| 8,368,027 B2 | 2/2013 | Ishii et al. | |
| 8,519,344 B2 | 8/2013 | Ishii et al. | |
| 8,680,472 B2 | 3/2014 | Mochizuki et al. | |
| 8,878,972 B2 | 11/2014 | Wayama et al. | |
| 9,270,903 B2 | 2/2016 | Wayama et al. | |
| 9,277,896 B2 | 3/2016 | Ofuji et al. | |
| 9,423,513 B2 | 8/2016 | Watanabe et al. | |
| 9,521,347 B2 | 12/2016 | Kawanabe et al. | |
| 9,625,585 B1 | 4/2017 | Yokoyama et al. | |
| 9,726,767 B2 | 4/2017 | Kawanabe et al. | |
| 9,661,240 B2 | 5/2017 | Fujiyoshi et al. | |
| 9,675,307 B2 | 6/2017 | Ofuji et al. | |
| 9,835,732 B2 | 12/2017 | Fujiyoshi et al. | |
| 9,838,638 B2 | 12/2017 | Furumoto et al. | |
| 9,948,871 B2 | 4/2018 | Wayama et al. | |
| 9,977,135 B2 | 5/2018 | Yokoyama et al. | |
| 10,068,943 B2 | 9/2018 | Fujiyoshi et al. | |
| 10,473,801 B2 | 11/2019 | Kawanabe et al. | |
| 10,537,295 B2* | 1/2020 | Watanabe | A61B 6/542 |
| 10,634,800 B2 | 4/2020 | Yokoyama et al. | |
| 10,653,372 B2 | 5/2020 | Wayama et al. | |
| 2012/0132824 A1* | 5/2012 | Nishino | H04N 5/32 |
| | | | 250/394 |
| 2013/0342514 A1 | 12/2013 | Yokoyama et al. | |
| 2014/0151769 A1 | 6/2014 | Wayama et al. | |
| 2014/0154833 A1 | 6/2014 | Wayama et al. | |
| 2015/0316661 A1* | 11/2015 | Fujiyoshi | H01L 27/14663 |
| | | | 250/366 |
| 2015/0319382 A1* | 11/2015 | Kawanabe | G01T 1/17 |
| | | | 378/62 |
| 2016/0041276 A1* | 2/2016 | Kawanabe | G01T 1/17 |
| | | | 378/62 |
| 2019/0146103 A1 | 3/2019 | Ofuji et al. | |
| 2019/0391629 A1 | 12/2019 | Yokoyama et al. | |
| 2020/0008766 A1 | 1/2020 | Watanabe et al. | |
| 2020/0041664 A1 | 2/2020 | Furumoto et al. | |
| 2020/0060639 A1 | 2/2020 | Sato et al. | |
| 2020/0124749 A1 | 4/2020 | Takenaka et al. | |
| 2020/0166659 A1 | 5/2020 | Fujiyoshi et al. | |

FOREIGN PATENT DOCUMENTS

| | | | |
|---|---|---|---|
| JP | 2016-220116 | 12/2016 | |
| WO | WO-2016189788 A1 * | 12/2016 | ....... H01L 31/02322 |

* cited by examiner

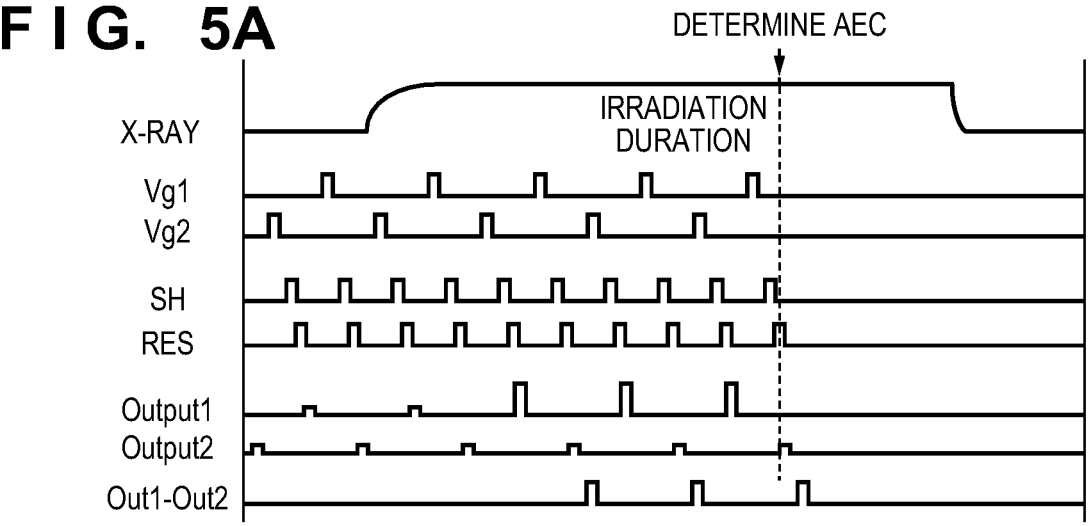
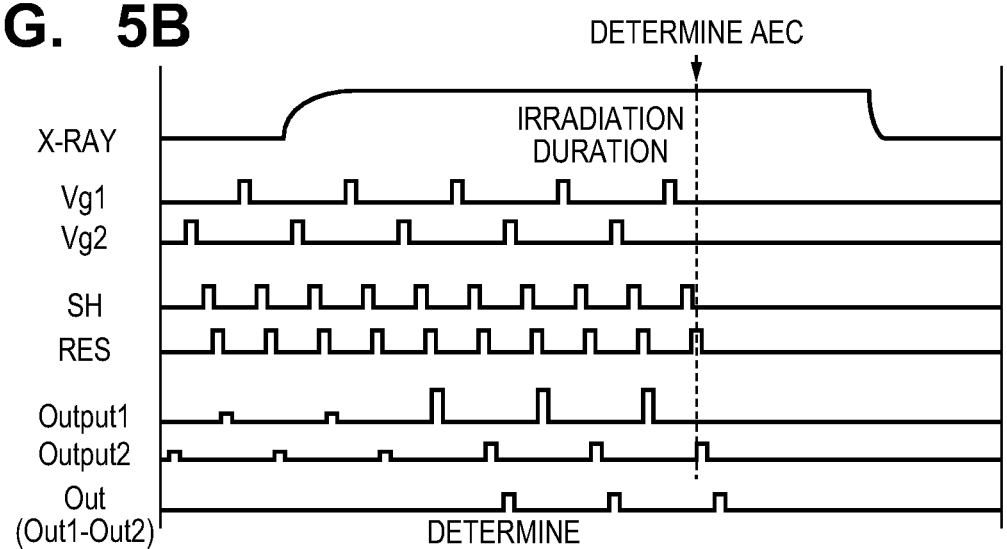
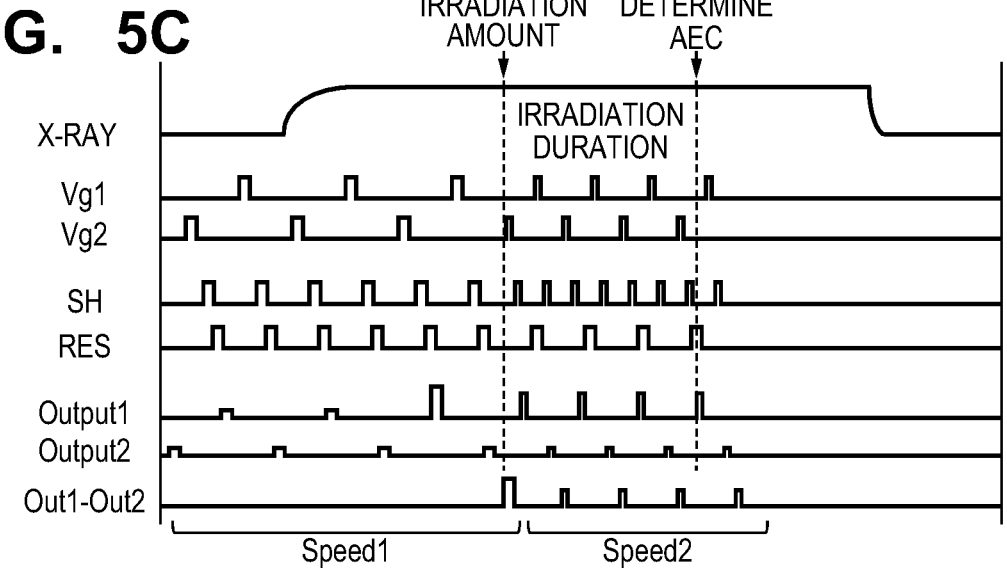

RADIATION IMAGING APPARATUS AND RADIATION IMAGING SYSTEM

CROSS-REFERENCE TO RELATED APPLICATIONS

This application is a Continuation of International Patent Application No. PCT/JP2018/043952, filed Nov. 29, 2018, which claims the benefit of Japanese Patent Application No. 2018-029053, filed Feb. 21, 2018, both of which are hereby incorporated by reference herein in their entirety.

BACKGROUND OF THE INVENTION

Field of the Invention

The present invention relates to a radiation imaging apparatus and a radiation imaging system.

Background Art

A radiation detection apparatus has been utilized which combines an imaging region in which pixels for acquiring a radiation image, conversion elements each of which converts radiation into an electric signal, switching elements such as thin film transistors, and the like are two-dimensionally arranged, a drive circuit, and a readout circuit. As such a radiation detection apparatus, it has been considered to incorporate a function of detecting irradiation information into the radiation detection apparatus. This function is a function of detecting an incident start timing of radiation applied from a radiation source and detecting the irradiation amount and accumulated irradiation amount of radiation. This function also enables automatic exposure control (AEC) in which the accumulated irradiation amount is monitored, and when the accumulated irradiation amount reaches an appropriate amount, the detection apparatus controls the radiation source to terminate the irradiation.

The radiation detection apparatus may include a scintillator that converts radiation into light and a photoelectric conversion element. In a case in which a signal from the photoelectric conversion element (photoelectric conversion element for detection) for measuring the start of radiation irradiation, the irradiation amount, and the accumulated irradiation amount is read out through a signal line, the signal line is wired in the vicinity of a pixel including a photoelectric conversion element (photoelectric conversion element for an image) for acquiring a captured image of radiation. Therefore, a non-negligible capacitance is formed between the signal line and the pixel for acquiring a captured image. Due to this capacitance, even when only the information from the photoelectric conversion element for detection is desired to be obtained, a signal from the photoelectric conversion element for an image is transmitted to the signal line via the capacitance (to be referred to as crosstalk hereinafter), so that it is difficult to accurately measure a measurement value for radiation detection. In addition, when a thin film transistor or a photoelectric conversion element is used in the radiation detection element, characteristics such as leakage current and dark current change when the temperature changes. Similarly, when the temperature changes, the offset level characteristic or the like generated when the thin film transistor or the photoelectric conversion element is driven changes.

A radiation imaging apparatus described in PTL 1 includes a first detection element and a second detection elements each of which converts radiation into an electric signal, the first detection element being connected to a first signal line and the second detection element being connected to a second signal line. PTL 1 discloses that based on a signal from the first detection element output via the first signal line and a signal from the second detection element output via the second signal line, the influence of crosstalk and a change in characteristics caused by the temperature are corrected.

However, it has been found that the method in PTL 1 has a limit in correcting the influence of crosstalk because the amount of crosstalk affecting the first signal line and the amount of crosstalk affecting the second signal line are different.

CITATION LIST

Patent Literature

PTL 1: Japanese Patent Laid-Open No. 2016-220116

SUMMARY OF THE INVENTION

In order to solve the problem described above, there is provided a radiation imaging apparatus comprising an imaging region including a plurality of detection elements each including a conversion element configured to convert radiation into an electric signal, a first signal line, and a signal processing circuit configured to process a signal output via the first signal line, wherein the plurality of detection elements include a first detection element and a second detection element which are connected to the first signal line, a sensitivity of the first detection element to radiation is set to be different from a sensitivity of the second detection element to radiation, and the signal processing circuit generates information related to irradiation of radiation to the imaging region based on signals from the first detection element and the second detection element which are connected to the first signal line.

Further features of the present invention will become apparent from the following description of exemplary embodiments with reference to the attached drawings.

BRIEF DESCRIPTION OF THE DRAWINGS

The accompanying drawings are included in and constitute a part of the specification, illustrate embodiments of the present invention and, together with the description, serve to explain the principles of the present invention.

FIG. 5A is a timing chart according to the first embodiment of the present invention.

FIG. 5B is a timing chart according to the first embodiment of the present invention.

FIG. 5C is a timing chart according to the first embodiment of the present invention.

DESCRIPTION OF THE EMBODIMENTS

Figure 1:
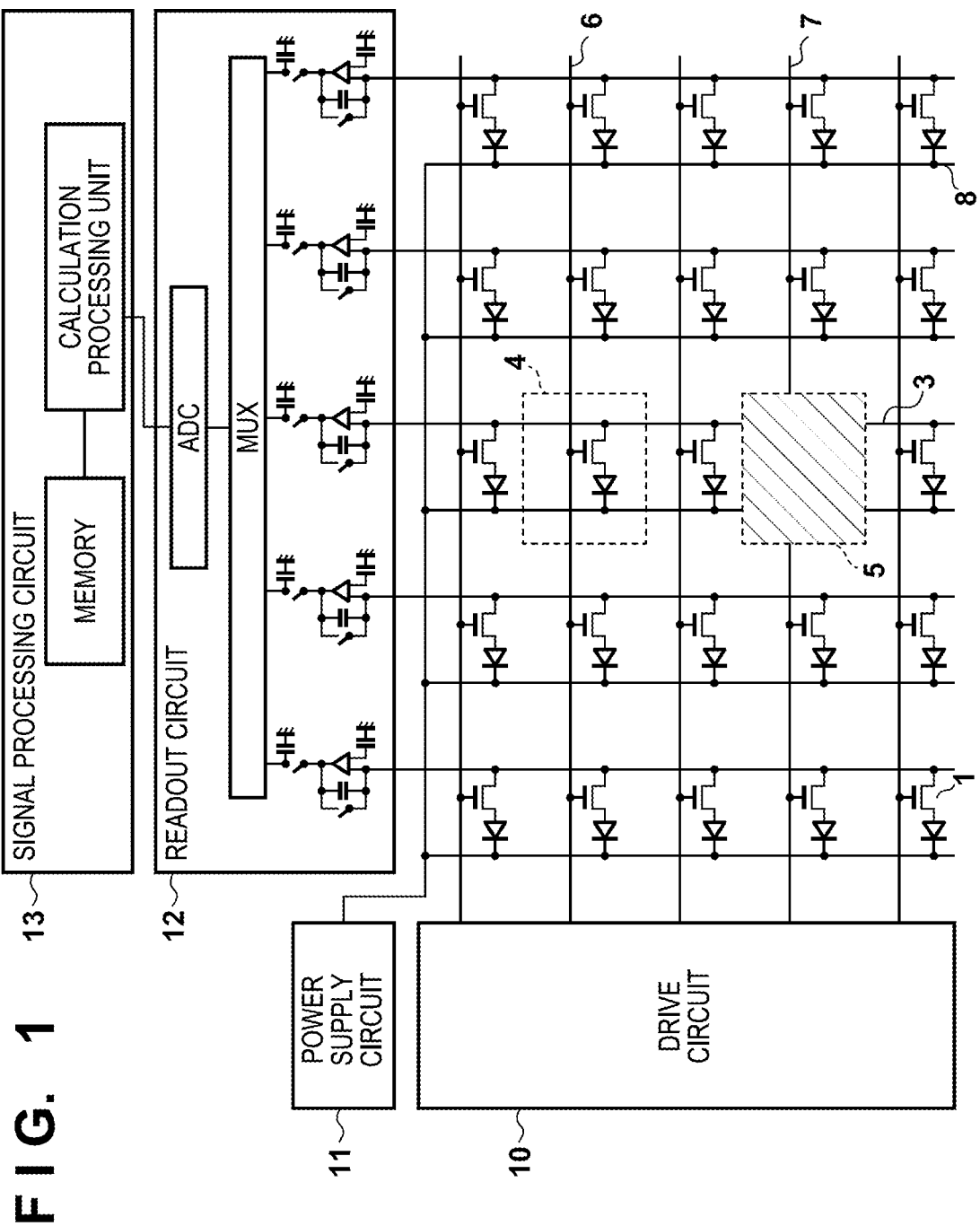
FIG. 1 is an equivalent circuit diagram of a radiation imaging apparatus according to the first embodiment of the present invention.

Hereinafter, embodiments of the present invention will be specifically explained with reference to the accompanying drawings. Note that radiation in this application specification includes α-rays, β-rays, γ-rays, and the like which are beams generated by particles (including photons) emitted by radiation decay, as well as beams having the same or higher energy, for example, X-rays, particle beams, cosmic rays, and the like. Electromagnetic waves are those in the wavelength range from light such as visible light and infrared light to radiation such as X-rays, α-rays, β-rays, and γ-rays.

First Embodiment

First, the first embodiment of the present invention will be described with reference to FIG. 1. A radiation imaging apparatus in this embodiment includes an imaging region in which pixels 1, a detection element 4 for radiation detection, and a correction element 5 for correction are arranged in a matrix on a substrate. The radiation imaging apparatus further includes a readout circuit 12 for reading a signal from a signal line, a signal processing circuit 13 that processes a readout signal, a drive circuit 10 that provides a drive signal to a control line, and a power supply circuit 11.

FIG. 1 shows the pixels and the like arranged in five rows and five columns in the imaging region, but this shows merely a partial region in the radiation detection apparatus. The pixel 1 for acquiring an image, the detection element 4 for radiation detection used to measure the start of radiation irradiation and an irradiation amount, and the correction element 5 for correcting a signal from the detection element 4 are included in the imaging region. Each of the pixel 1, the detection element 4, and the correction element 5 includes a conversion element that converts radiation into an electric signal. An electric signal from the detection element 4 is used to detect irradiation or irradiation intensity (irradiation amount) of radiation to the imaging region during irradiation of radiation, or the start/end of radiation irradiation. By arranging such the detection element 4 in the imaging region, it is possible to incorporate an automatic exposure control (AEC) function into the radiation imaging apparatus.

In the actual radiation imaging apparatus, such the detection element 4 is included in a region obtained by dividing the imaging region into a matrix of 3×3 or 5×5, so that it is possible to detect, for each region, irradiation information of the radiation applied to each region. In addition, in order to increase the sensitivity of detecting the irradiation amount of the radiation applied to each region, pixel addition (binning) may be performed in which signals from a plurality of the detection elements 4 and a plurality of the correction elements 5 are added and read out. Thus, the two-dimensional layout is not limited to this embodiment. It is possible to change the number of pixels to be added, arbitrarily shift the arrangement position of the detection region, or increase the number of detection elements.

The pixel 1 and the detection element 4 can have almost the same structure. In this case, if the AEC function is used, the pixel 1 and the detection element 4 may be used for image acquisition and for irradiation amount measurement, respectively, and if the AEC function is not used, all the detection elements 4 may be used as the pixel 1 for image acquisition.

The detection element 4 can detect irradiation information during irradiation of radiation. The correction element 5 is an element that detects radiation to correct crosstalk included when an output from the detection element 4 is read out. The detection element 4 is driven using a first control line 6. When the detection element 4 is driven using the first control line 6, a signal is read out from the detection element 4, and the signal is transferred to the readout circuit 12 via a signal line 3. The correction element 5 is controlled using a second control line 7. When the correction element 5 is driven using the second control line 7, a signal is read out from the correction element 5 and the signal is transferred to the readout circuit 12 via the signal line 3.

In this example, a signal from the detection element 4 connected to the first control line 6 is corrected using a signal from the correction element 5 connected to the second control line 7. Note that the first control line 6 and the second control line 7 may be provided separately from the control line for controlling the pixel 1, and the detection element 4 and the correction element 5 may be driven separately from the pixel for an image.

When a signal from the detection element 4 is output, electric charges, which are generated by radiation applied to the entire surface or a partial surface, are also stored in the electrode of the conversion element included in the pixel 1. These electric charges are transmitted to the signal line 3 as a signal due to crosstalk via the parasitic capacitance between the electrode of the conversion element of the pixel 1 and the signal line 3 to which the detection element 4 is connected. Similarly, when an output from the correction element 5 is read out, a signal generated due to crosstalk is transmitted from the pixel 1 to the signal line 3 via the parasitic capacitance. Since these two signals each generated due to crosstalk are signals to the same signal line 3, they have almost the same amount. By obtaining the difference between the two signals from the detection element 4 and the correction element 5, it is possible to reduce the signal generated due to crosstalk in the signal from the detection element 4 for radiation detection. Further, by reading out signals from the detection element 4 and the correction element 5 using the same signal line, it is possible to reduce the influence of a variation in offset, a variation in gain, or the like of the elements in the path of the signal line.

In the example shown in FIG. 1, the detection element 4 and the correction element 5 are arranged so as to have a space for one pixel therebetween in the imaging region, but they may be arranged adjacent to each other in the direction of the signal line 3. In addition, a plurality of pairs each including the detection element 4 and the correction element 5 may be arranged in the direction of the signal line 3 at a constant interval, and the irradiation amount may be measured using data obtained by digital addition of the detection element and the correction element or a value obtained by analog addition thereof. In this case, a plurality of the first control lines 6 or a plurality of the second control lines 7 may be simultaneously driven to collectively output signals from a plurality of the detection elements 4 or a plurality of the correction elements to the signal line 3, respectively.

Further, in the example shown in FIG. 1, the detection element 4 and the correction element 5 are formed in the same size as the pixel 1 for image acquisition. However, the detection element 4 and the correction element 5 may be formed in a smaller size than the pixel 1 for image acquisition. In this case, by arranging the detection element 4 and the correction element 5 in a gap in the pixel 1, it is possible to reduce a defective portion of the image signal. Then, it is preferable to separately arrange the first control line 6 and the second control line 7 as dedicated lines for controlling the detection element 4 and the correction element 5, respectively. By arranging the dedicated lines, the detection element 4 and the correction element 5 can be controlled separately from the control of the pixel 1. Similarly, the signal line 3 may be arranged in the imaging region as a dedicated line for the detection element 4 and the correction element 5.

Figure 2A:
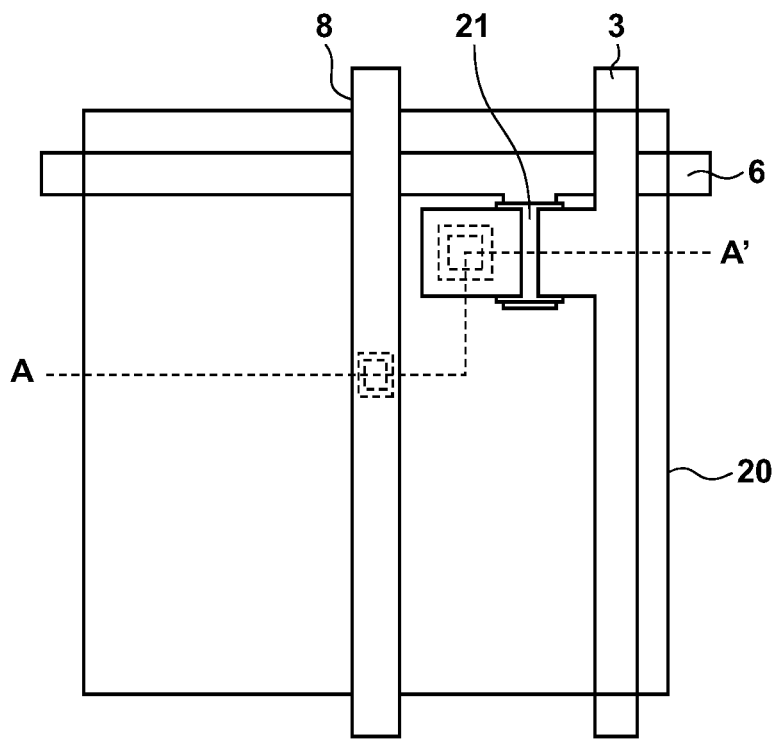
FIG. 2A is a schematic plan view showing a detection element for radiation detection according to the first embodiment of the present invention.

FIG. 2A is a plan view of the detection element 4 for radiation detection in this embodiment. A scintillator (not shown) that converts radiation into light is provided above the detection element 4. The light converted by the scintillator is converted into electric charges by the photoelectric conversion element and transferred to the signal line via a switch. A photoelectric conversion element 20 for detection, a thin film transistor (referred to as TFT hereinafter) 21, and various types of wirings such as a power supply line and the signal line are arranged in the detection element. A signal from the photoelectric conversion element 20 for detection is transferred to the signal line 3 via the TFT 21. ON/OFF of the TFT 21 is controlled using the control line 6. The upper electrode of the photoelectric conversion element 20 for detection is a common electrode 115 connected to a bias line 8 for applying a constant voltage. The lower electrode of the photoelectric conversion element 20 is an individual electrode 111 for each element. The signal line 3 extends to the readout circuit 12 in the imaging region, and has a portion that is two-dimensionally overlapped with the photoelectric conversion element for an image included in the pixel 1 for image acquisition. The photoelectric conversion element for an image has a structure similar to that of the photoelectric conversion element for detection, and the lower electrode is an individual electrode. With such a structure, a capacitance corresponding to the overlap area is formed between the individual electrode of the photoelectric conversion element for an image and the signal line 3. Electric charges stored in the photoelectric conversion element for an image are transmitted to the signal line 3 via the capacitance based on an electric charge conservation law, resulting in crosstalk.

In the above description, an example in which the photoelectric conversion element for an image and the signal line 3 overlap with each other has been described. However, even when they do not overlap with each other, if a parasitic capacitance spatially coupled to the photoelectric conversion element 20 for an image and the signal line 3 exists therebetween, crosstalk from the photoelectric conversion element 20 to the signal line 3 is generated.

Since the crosstalk is transmitted to the signal line 3 from each of all the pixels 1 capacitively coupled to the signal line 3, the signal amount is massive. As a result, a large error is generated when accurately reading out a signal from the detection element 4 connected to the signal line 3. This error can be relatively reduced by connecting a plurality of the detection elements 4 while arranging them in the imaging region in a scattered manner and increasing the signal amount from the detection elements 4. However, it is difficult to eliminate the error.

Figure 2B:
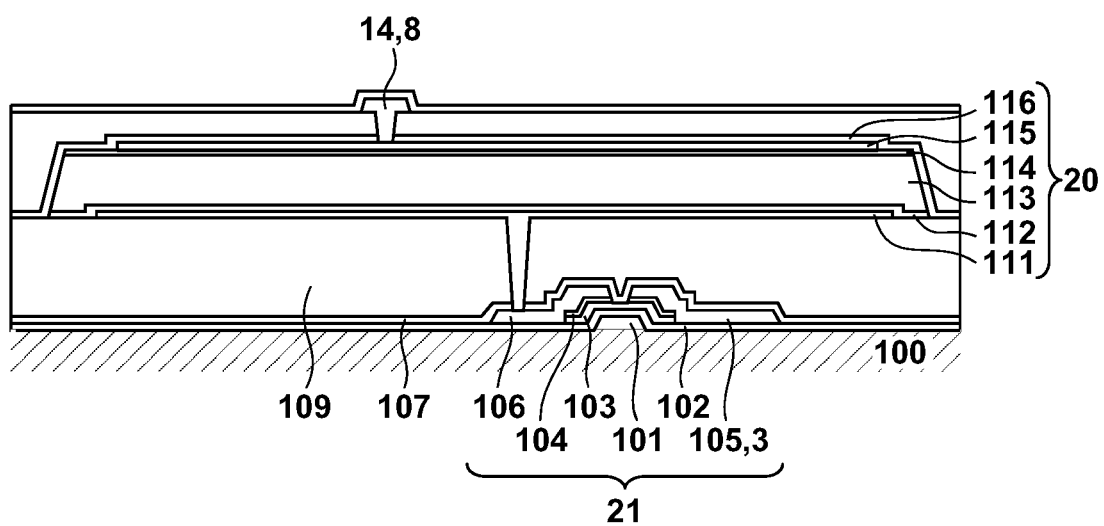
FIG. 2B is a schematic sectional view showing the detection element for radiation detection according to the first embodiment of the present invention.

FIG. 2B a sectional view taken along a line A-A' shown in FIG. 2A. The photoelectric conversion element 20 for detection is arranged in the upper part of FIG. 2B, and the TFT 21 as a switch for transferring electric charges stored in the photoelectric conversion element to the signal line 3 is arranged in the lower part of FIG. 2. In this embodiment, an insulating substrate such as a glass substrate or a plastic substrate is used as a substrate 100. The TFT 21 as a switch element is formed on the substrate 100. The TFT 21 includes a gate electrode 101, a source electrode 105, a drain electrode 106, an insulating layer 102, a first semiconductor layer 103, and a first impurity semiconductor layer 104. The photoelectric conversion element 20 includes the individual electrode 111, a second impurity semiconductor layer 112, a second semiconductor layer 113, a third impurity semiconductor layer 114, the common electrode 115, and a protective film 116. The drain electrode 106 is connected to the individual electrode 111 by a contact. The common electrode 115 is connected to the bias line 8. The source electrode 105 of the TFT 21 forms a part of the signal line 3, and when the TFT 21 is turned on, electric charges of the photoelectric conversion element 20 are transferred to the signal line 3 as an electric signal.

FIGS. 2A and 2B show the detection element 4. However, the positional relationship between the signal line 3 and the photoelectric conversion element 20 is similar to that of the photoelectric conversion element of the pixel 1, so that the parasitic capacitance between the pixel 1 and the signal line 3 will be described with reference to FIG. 2B. A thick insulating film 109 is arranged between the individual electrode 111 in the lower portion of the photoelectric conversion element 20 and the signal line 3 (source electrode 105). This insulating film reduces the parasitic capacitance formed between the individual electrode 111 and the signal line 3 (source electrode 105). However, there is a parasitic capacitance corresponding to the dielectric constant, the thickness, and the area of the insulating film, and a signal generated due to crosstalk caused by the parasitic capacitance is transmitted from the individual electrode 111 to the signal line 3 (105). Even if the individual electrode 111 and the signal line 3 (105) do not vertically overlap with each other and are arranged at horizontally shifted positions, it is difficult to eliminate the parasitic capacitance. The crosstalk generated based on the electric charges is written in the signal line 3 (105) by an amount corresponding to the parasitic capacitance. Therefore, the correction element 5 is used to correct the crosstalk.

Figure 3A:
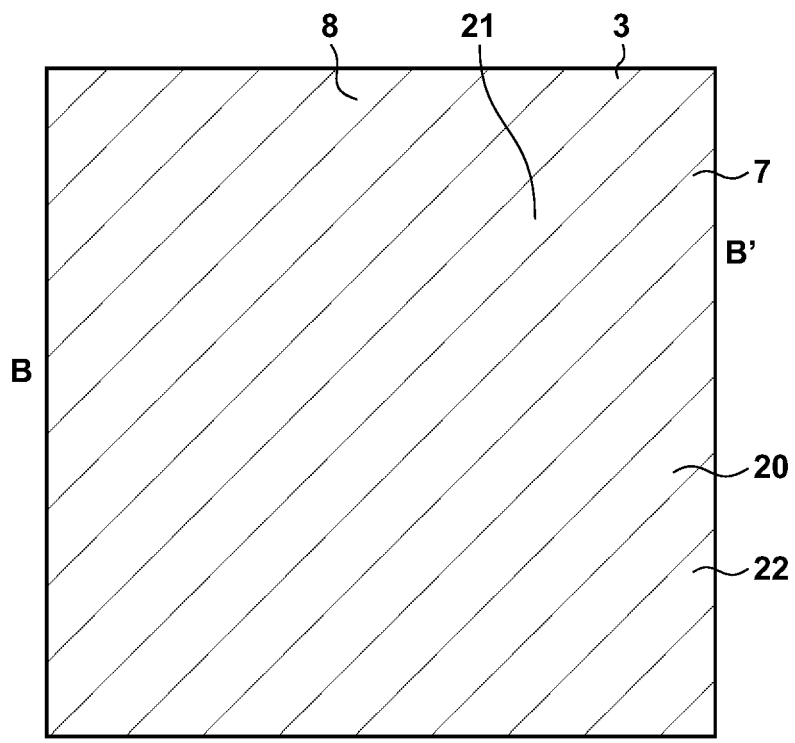
FIG. 3A is a schematic plan view showing a correction element according to the first embodiment of the present invention.

FIG. 3A is a plan view of the correction element 5 in this embodiment. FIG. 3A shows the TFT 21, the photoelectric conversion element 20 arranged above the TFT 21, and a light shielding region 22 formed above the photoelectric conversion element 20.

Figure 3B:
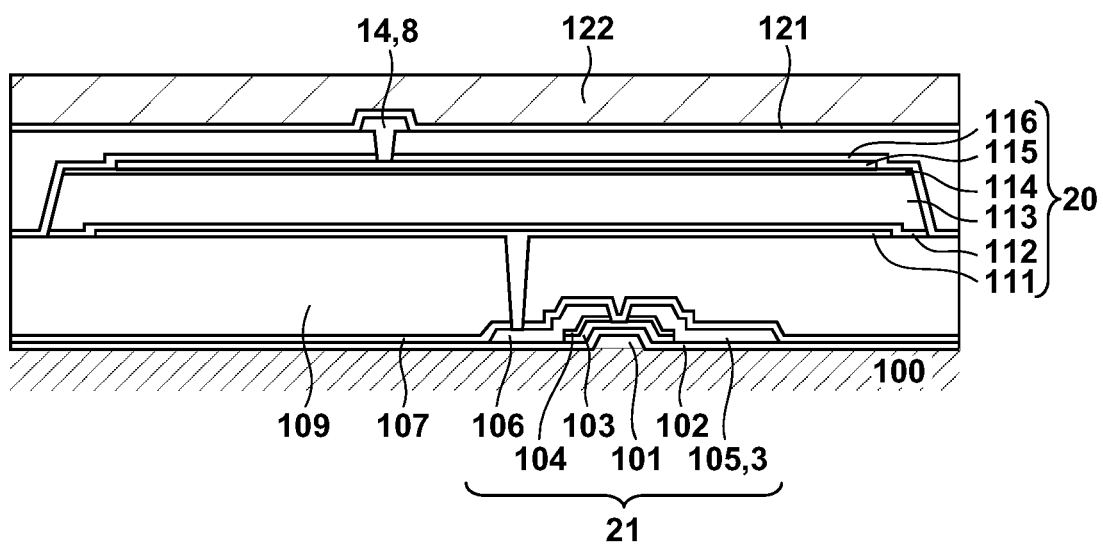
FIG. 3B is a schematic sectional view showing the correction element according to the first embodiment of the present invention.

FIG. 3B is a sectional view taken along a line B-B' shown in FIG. 3A. The light shielding region 22 shown in FIG. 3A corresponds to a light shielding layer 122 shown in FIG. 3B. As a light shielding member forming the light shielding layer 122, it is preferable to use an organic film of a color such as black or red that has a role of shielding visible light having a wavelength to which the photoelectric conversion element 20 is sensitive. Further, when arranging the light shielding region, it is preferable to use a material having a photosensitivity and perform arrangement by a photolithography method so that the arrangement accuracy can be secured. Furthermore, it is desirable that the photoelectric conversion element 20 is completely covered to prevent leakage light. When a bias line 14 is formed by a metal film having a light shielding property, it is preferable to cover the entire surface of the photoelectric conversion element 20 with the bias line 14 and use it as the light shielding member without newly forming an organic film so that the correction element can be formed without increasing the number of processes.

Figure 4A:
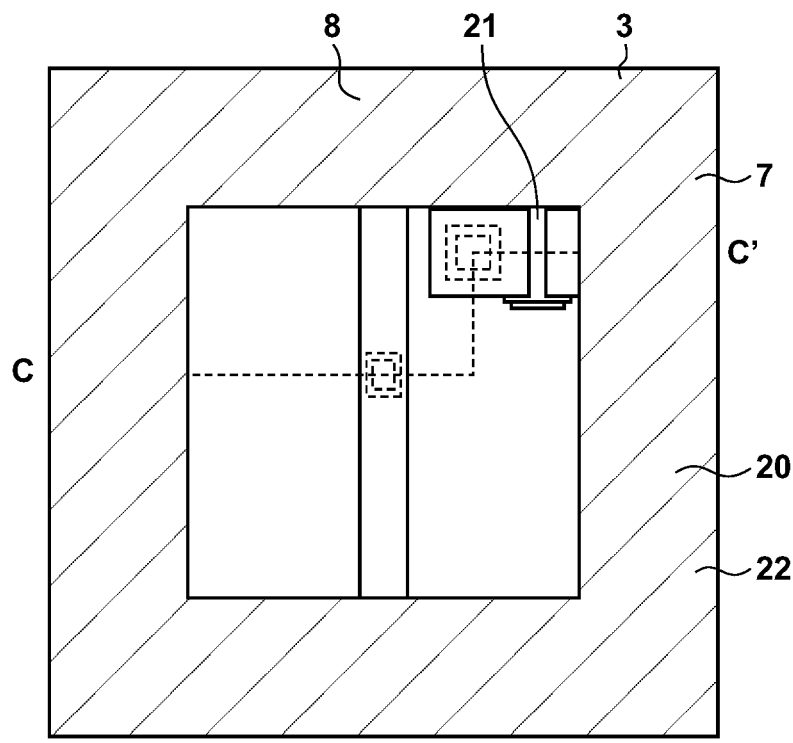
FIG. 4A is a schematic plan view showing the correction element according to the first embodiment of the present invention.

FIG. 4A is a view showing another example of the correction element in the first embodiment of the present invention. The light shielding region 22 formed above the correction element has a partial opening. Compared to FIG. 3A, the correction element 5 has a sensitivity to radiation and generates a signal. However, the sensitivity is lower than that of the detection element 4, so that it is possible to eliminate crosstalk by obtaining a difference output.

Figure 4B:
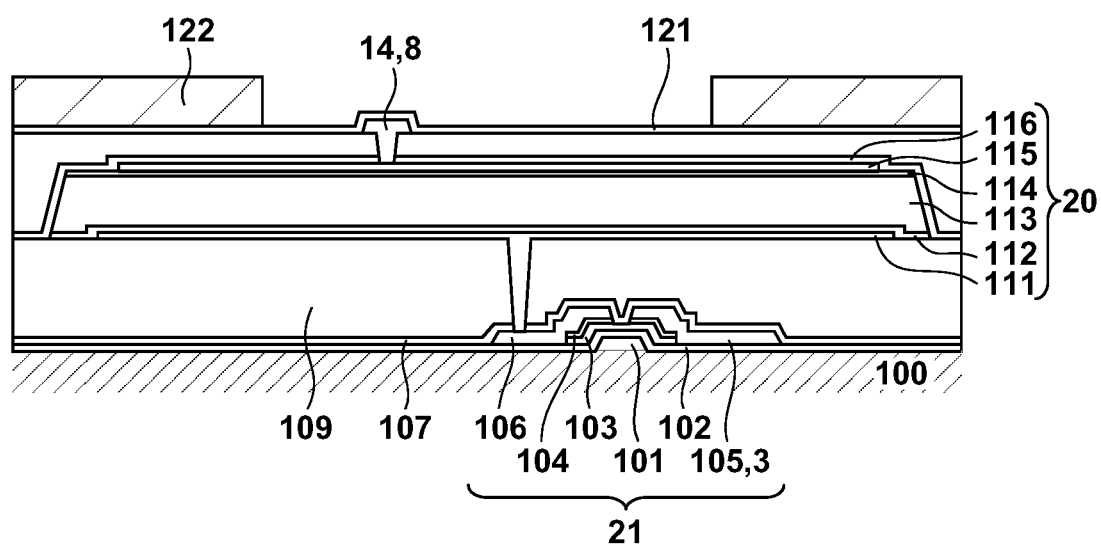
FIG. 4B is a schematic sectional view showing the correction element according to the first embodiment of the present invention.

FIG. 4B is a sectional view taken along a line C-C' shown in FIG. 4A. The light shielding region 22 shown in FIG. 4A corresponds to the light shielding layer 122 shown in FIG. 4B. Unlike in FIG. 3B, the light shielding layer 122 includes a partial opening in this example. In some cases, the detection accuracy improves when a certain opening is provided in the light incident surface of the correction element 5. When an output from the correction element 5 is extremely small so a good linearity characteristic cannot be obtained with the photoelectric conversion element, the linearity of an output from the correction element 5 improves by providing a certain opening and slightly discharging the output. As a result, the crosstalk amount can be reduced, and the measurement accuracy of the radiation dose obtained from the difference between the detection element 4 and the correction element 5 improves. As in the example shown in FIGS. 3A and 3B, when the bias line 14 is formed by a metal film having a light shielding property, a light shielding region that covers the photoelectric conversion element 20 while providing an opening is formed using the wiring material of the bias line 14 without forming a light shielding layer of an organic film. It is preferable to utilize the wiring material for the bias line so that the correction pixel can be formed without increasing the number of processes.

FIG. 5A is a timing chart in an example using the correction element shown in FIGS. 3A and 3B. The drive circuit 10 provides signals for driving the detection element and the correction element to the first control line 6 and the second control line 7, respectively. Vg1 indicates a drive signal applied to the first control line 6, and Vg2 indicates a drive signal applied to the second control line 7. Further, SH indicates a sample hold operation, RES indicates a reset operation for resetting electric charges stored in the IC and the line, Output1 indicates a signal read out from the detection element 4, and Output2 indicates a signal read out from the correction element 5. In this example, an output Out which is finally read out is the difference obtained by subtracting Output2 from Output1. Since the drive signals Vg1 and Vg2 are sequentially applied to the control lines from the drive circuit 10 even before radiation enters, it is possible to detect the incident timing of radiation. The signal output to the signal line 3 before irradiation of radiation serves as an offset component generated in each of the detection element 4 and the correction element 5. Since no radiation is being applied, Output1 and Output2 have almost the same amount, and a difference output (Out1−Out2) is almost zero.

When radiation enters, a large amount of electric charges is generated in the detection element 4. Since the correction element 5 is shielded from light, electric charges corresponding to the offset are generated. By sequentially reading out their signals using the control signals Vg1 and Vg2 and outputting the difference (Out1−Out2), it becomes possible to accurately know the start of radiation irradiation. In addition, it is possible to accurately read out the radiation irradiation amount, and it is also possible to obtain the integrated dose. When reading out the signal, the amount of crosstalk generated in the signal line 3 is added to each of the outputs from the detection element and the correction element, and the output becomes higher than that obtained when no radiation is being applied. However, the crosstalk amount in the signal line 3 when reading out the signal from the detection element 4 and the crosstalk amount in the signal line 3 when reading out the signal from the correction element 5 are almost equal to each other since they are read out in almost the same time period. Therefore, it is possible to remove the crosstalk amount by subtraction.

Information related to radiation irradiation is generated based on the difference output (Out1−Out2). Based on the generated information, the incident timing of radiation may be detected, or irradiation may be stopped by detecting that a predetermined irradiation amount has been reached. When used as the AEC, the accumulated radiation dose is predicted based on the generated information. Then, a determination may be performed at the predicted radiation stop timing and a preparation for a readout operation from the pixel for an image may be started.

As has been described above, by setting such that the detection element and the correction element have different sensitivities to radiation, the signal from the detection element is corrected using the signal obtained from the correction element. When a photoelectric conversion element is used as the conversion element, correction can be performed by setting the sensitivity of the correction element to electromagnetic waves to be lower than the sensitivity of the detection element to electromagnetic waves. The method of lowering the sensitivity is not limited to providing the light shielding portion. The sensitivity may be adjusted to be low by decreasing the bias voltage applied to the photoelectric conversion element of the correction element.

FIG. 5B is a timing chart in an example using the correction element shown in FIGS. 4A and 4B, which is partially shielded from light. When radiation enters, a large amount of charges are generated in the detection element 4 and a small amount of charges are generated in the correction element 5. By sequentially reading out their signals using the control signals Vg1 and Vg2 and outputting the difference (Out1−Out2), it becomes possible to accurately know the start of radiation irradiation. In addition, it is possible to accurately read out the radiation irradiation amount. By acquiring, in advance, information of the relationship between the difference output between the detection element and the correction element and the irradiation dose, it is also possible to obtain the integrated dose. In this example, the correction element has a certain sensitivity, so that it is possible to prevent a decrease in correction accuracy caused by the influence of a deterioration in linearity characteristic at the time of a low output, which occurs when the pixel has no sensitivity.

Another example of driving the detection element 4 and the correction element 5 of this embodiment by the drive circuit 10 will be described with reference to FIG. 5C. The correction element shown in FIGS. 3A and 3B is used. When it can be determined that the radiation irradiation amount is large at the radiation irradiation start stage so that a sufficient SNR and a sufficient sensitivity are obtained, the interval of sampling that is periodically performed can be shortened to improve the time resolution. Therefore, the irradiation amount is first determined by sampling with a certain cycle (Speed1), and if a sufficient sensitivity is obtained, the cycle of turning on/off the control line is shortened (Speed2) to increase the time resolution of sampling. When the time resolution is increased, the time in which electric charges generated by radiation irradiation are stored in the detection element 4 is shortened, so that the amount of generated electric charges becomes small. Similarly, the amount of crosstalk generated when reading out a signal from each of the detection element 4 and the correction element 5 also becomes small, but the radiation irradiation amount can be accurately corrected and read out by calculating the difference between the signals from detection element 4 and the correction element 5. Further, by increasing the time resolution, it is possible to improve the determination accuracy of the irradiation amount.

When the driving speed of the TFT or the storage time of the photoelectric conversion element is changed, the offset generated from the TFT, the dark current generated from the photoelectric conversion element, or the like changes. Further, the offset output may change with time. However, by driving the detection element 4 and the correction element 5 connected to the same signal line with the same cycle, the amount of the offset component such as the offset or dark current and the amount of its change over time becomes the same between these elements, so that it is possible to perform accurate correction by subtraction.

As an example of changing the driving speed, the example in which the time resolution is increased when the radiation irradiation amount is large has been described. However, when the radiation irradiation amount is small, the driving speed may be decreased to store electric charges in the photoelectric conversion element. Further, when a large number of detection elements are arranged in the radiation imaging apparatus, the detection element to be subjected to readout may be limited to one in the region from which a signal is to be read out, and the driving speed may be changed to further improve the time resolution. When switching the driving speed, the driving speeds of the first control line 6 and the second control line 7 are switched together. By changing the driving speed at the timing at which the offset or crosstalk amount at the time of reading out from the detection element 4 and the offset or crosstalk amount at the time of reading out from the correction element 5 become the same, it is possible to perform accurate correction.

Second Embodiment

Next, the second embodiment of the present invention will be described. Note that the description of parts similar to those in the first embodiment will be omitted. A radiation detection apparatus according to the second embodiment will be described with reference to FIG. 6. The second embodiment is different from the first embodiment in that there are a plurality of pairs each including a detection element 4 and a correction element 5, and respective pairs are connected to different signal lines.

Figure 6:
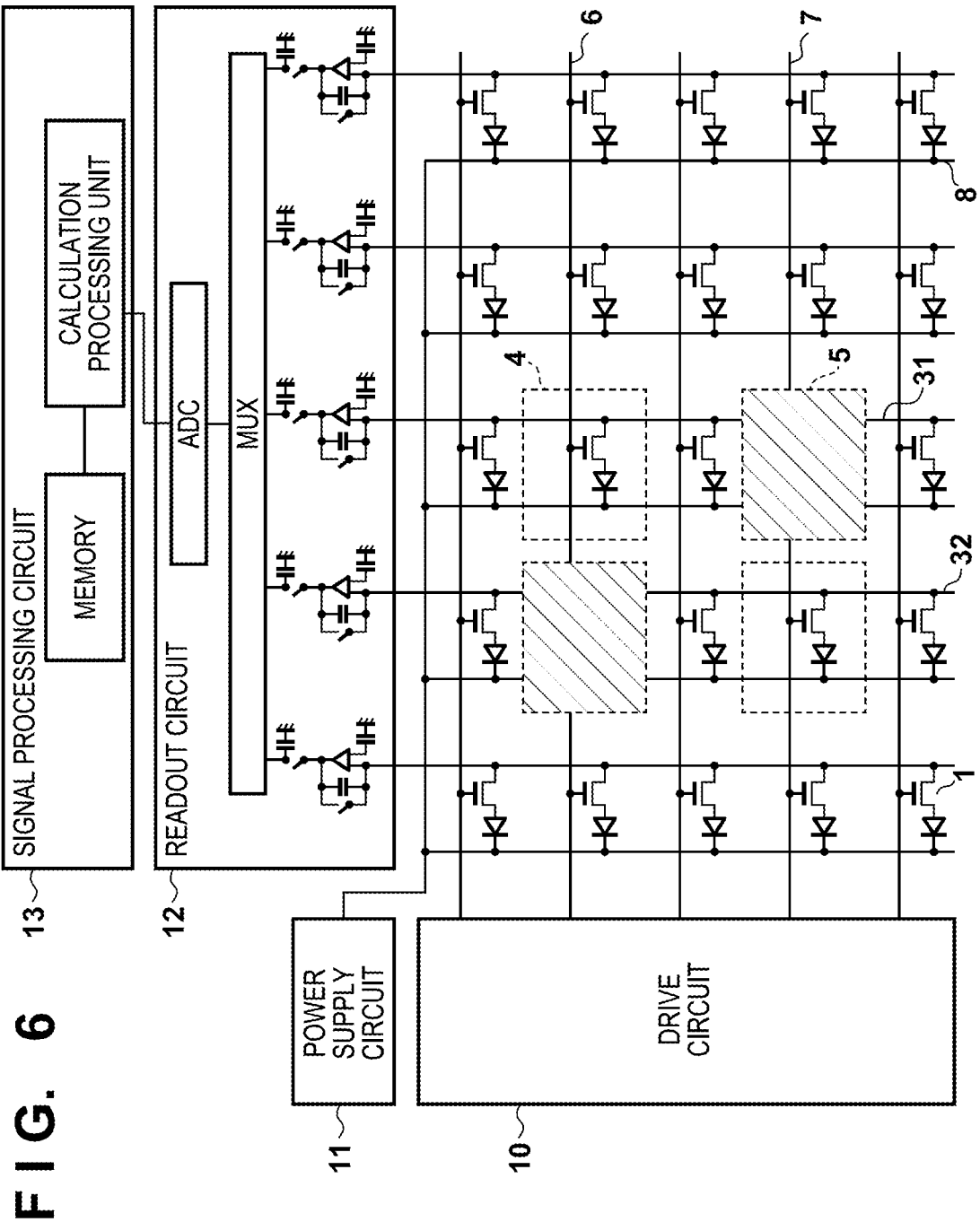
FIG. 6 is an equivalent circuit diagram of a radiation imaging apparatus according to the second embodiment of the present invention.

As shown in FIG. 6, the first detection element 4 and the first correction element 5 are connected to a first signal line 31. The second correction element 5 is arranged adjacent to the left side of the first detection element 4 in the same row, and the second detection element 4 is arranged adjacent to the left side of the first correction element 5. The second detection element 4 and the second correction element 5 are connected to a same second signal line 32. The detection element 4 and the correction element 5 arranged in the same row are controlled using the same control line. When a first control line 6 is driven, a signal from the first detection element 4 and a signal from the second correction element 5 arranged in the same row are simultaneously transferred to the readout circuit. Similarly, when a second control line 7 is driven, a signal from the first correction element 5 and a signal from the second detection element 4 arranged in the same row are simultaneously transferred to the readout circuit. By outputting the difference between the signals from the same signal line, two signals having different radiation irradiation times can be read out. Since the double signals can be obtained in the same readout time length, the time resolution can be doubled.

In this embodiment, pixels 1, the detection element 4, and the correction element 5 arranged in one row connected to the first control line 6 are simultaneously driven, and the pixels 1, the detection element 4, and the correction element 5 arranged in one row connected to the second control line 7 are simultaneously driven. However, the first control line 6 and the second control line 7 may be provided separately from a control line for controlling the pixel, and the detection element 4 and the correction element 5 may be driven separately from the pixel.

In the example shown in FIG. 6, in a case in which the output of the radiation source is small so that a leading pulse is widened and rises slowly, it is possible to perform effective correction for reducing crosstalk by correction based on a time difference. When a signal rises slowly, since the timing of reading out a signal from the detection element 4 and the timing of reading out a signal from the correction element 5 are different, the crosstalk amount is different therebetween and the correction accuracy decreases. In such a case, by increasing the time resolution, it is possible to prevent a decrease in correction accuracy. Further, by averaging the signals read out temporally before and after, it is possible to reduce an error even when radiation rises slowly. The time difference output of signals in the right column and the time difference output of signals in the left column may be shifted by a half cycle in time by shifting the timing of driving each control line, or may be simultaneously read out but recognized as outputs from different time zones.

Figure 7:
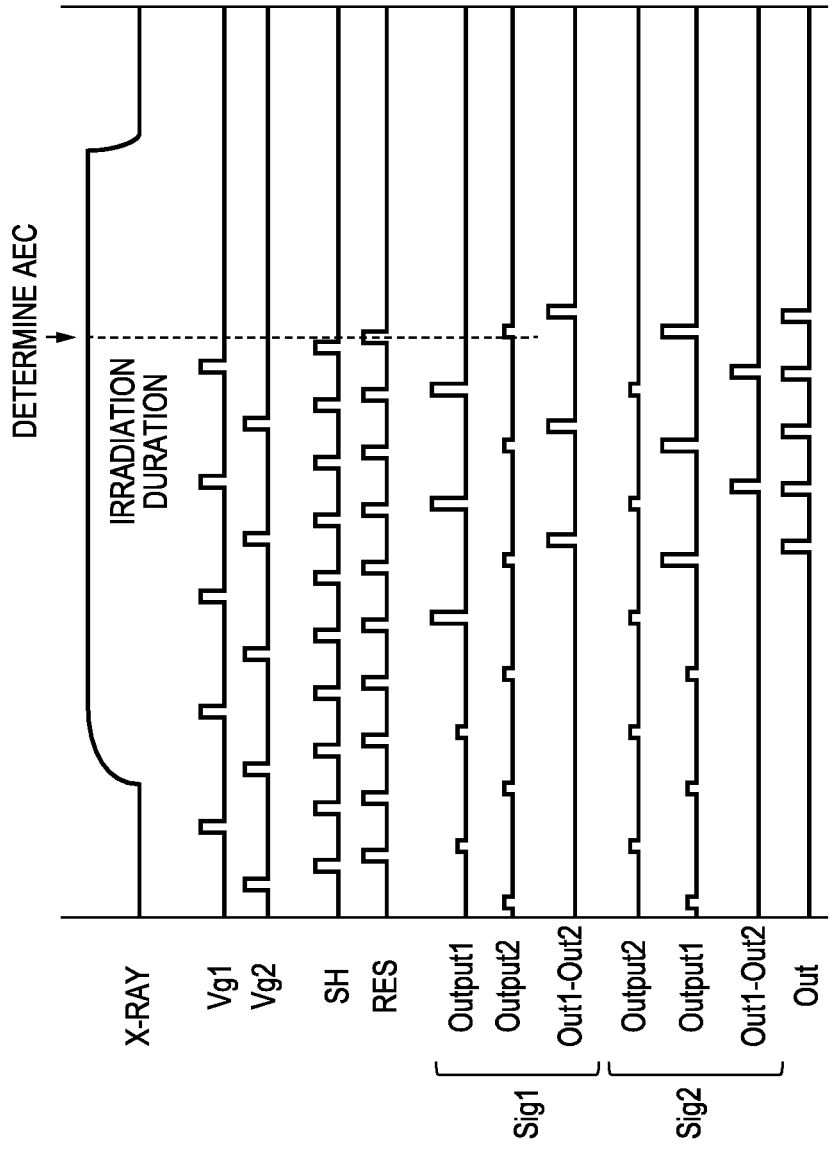
FIG. 7 is a timing chart according to the second embodiment of the present invention.

The operation will be described with reference to a timing chart shown in FIG. 7. The correction element shown in FIG. 3 is used. Here, Vg1 indicates a drive signal applied to the first control line 6, and Vg2 indicates a drive signal applied to the second control line 7. Further, SH indicates a sample hold operation, Output1 indicates a signal read out from the detection element 4, and Output2 indicates a signal read out from the correction element 5. The final readout output in each of the left and right columns is represented as a difference (Out1−Out2) obtained by subtracting Output2 from Output1. Sig1 represents how signals are read out from the first detection element and the first correction element in the right column in FIG. 6, and Sig2 represents how signals are read out from the second correction element 5 and the second detection element 4 in the left column. For both the left and right columns, the difference (difference between Out1 and Out2) between the output from the detection element 4 and the output from the correction element 5 read out thereafter is read out as Out1−Out2. By obtaining the sum of Out1–Out2 from Sig1 and Out1–Out2 from Sig2, it is possible to output a signal Out with the double time resolution of the example shown in FIGS. 5A and 5B. In this manner, by arranging the detection element 4 and the correction element 5 in pairs on the same control line, and in pairs on the same signal line, it is possible to increase the time resolution and improve the correction accuracy.

(Implementation)

Figure 8A:
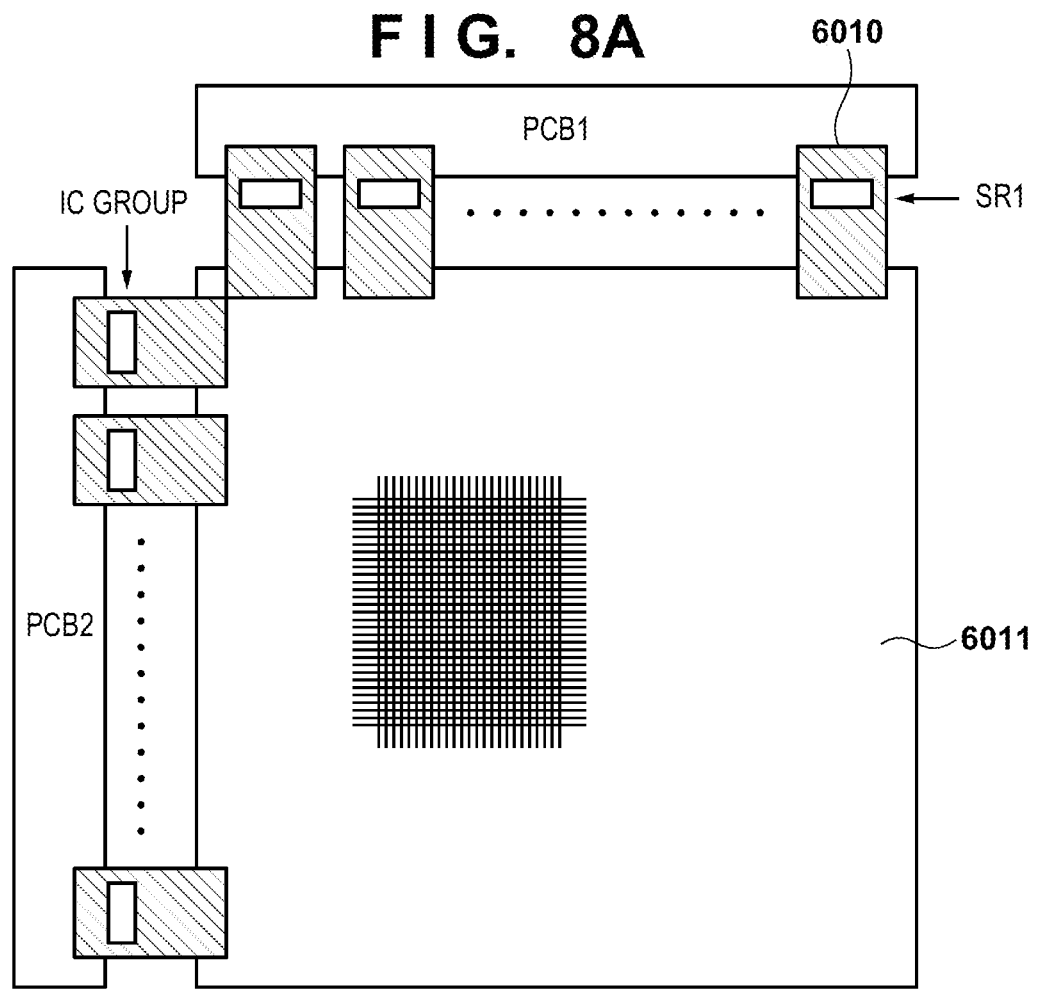
FIG. 8A is a schematic plan view showing a mounting example of the radiation imaging apparatus according to the present invention.
Figure 8B:
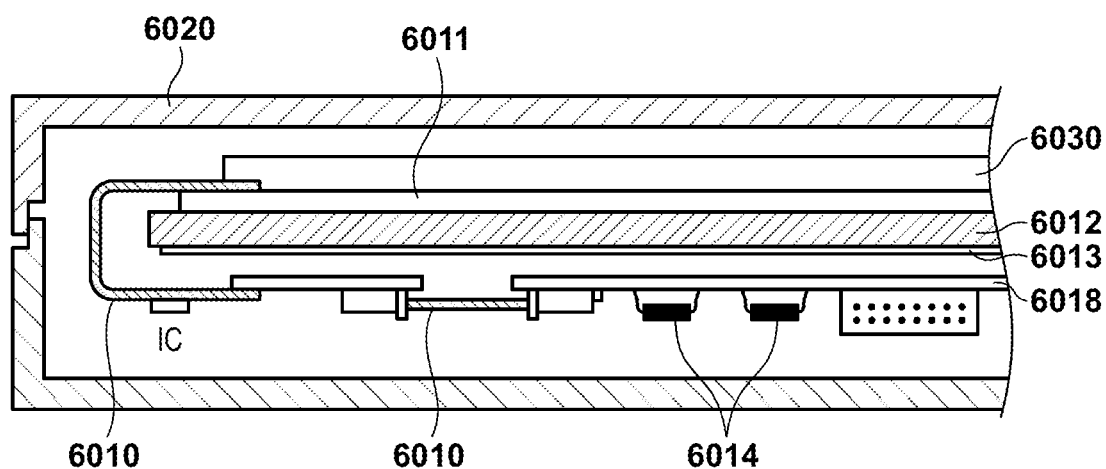
FIG. 8B is a schematic sectional view showing the mounting example of the radiation imaging apparatus according to the present invention.

Next, an implementation of the radiation imaging apparatus will be described with reference to FIGS. 8A and 8B. A plurality of photoelectric conversion elements and TFTs are formed in a sensor board 6011, and flexible circuit boards 6010, each of which is mounted with one of a shift register SR1 and an integrated circuit IC for detection, are connected thereto. The side of the flexible circuit board 6010 opposite to the side to which the sensor board 6011 is connected is connected to one of circuit boards PCB1 and PCB2. A plurality of the sensor boards 6011 are bonded to one surface of a base 6012 to form a large photoelectric conversion apparatus. A lead plate 6013 is mounted on the other surface of the base 6012 to protect a memory 6014 in a processing circuit 6018 from X-rays. A scintillator (phosphor layer) 6030 (formed of CsI or the like) for converting X-rays into visible light is deposited on the sensor board 6011. The whole is accommodated in a carbon fiber case 6020.

Figure 9:
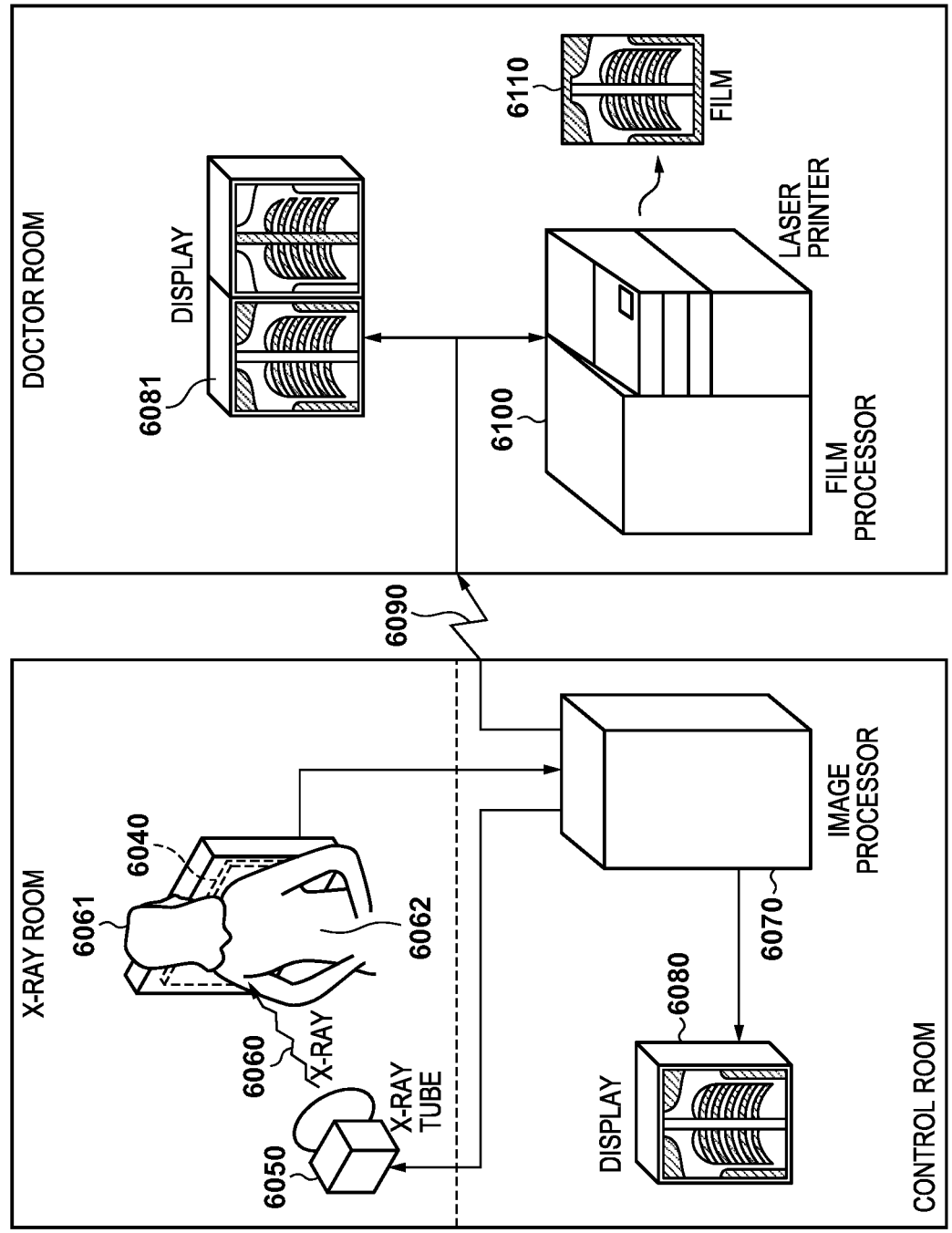
FIG. 9 is a schematic view showing a radiation imaging system.

Next, a radiation imaging system incorporating the radiation detection apparatus according to the present invention will be exemplarily described with reference to FIG. 9. X-rays 6060 generated in an X-ray tube 6050 are transmitted through a chest 6062 of a patient or subject 6061 and enter an image sensor 6040 with a scintillator (phosphor layer) mounted therein. This incident X-rays include information of the inside of the body of the patient 6061. The scintillator emits light in accordance with the entry of X-rays. A radiation imaging apparatus included in the image sensor photoelectrically converts this light by the photoelectric conversion element of the radiation imaging apparatus to obtain electrical information. This information undergoes digital conversion, further undergoes image processing by an image processor 6070 serving as a signal processing unit, and is provided for observation on a display 6080 serving as a display apparatus in the control room. Further, this information can be transferred to a remote place by a transmission processing apparatus such as a telephone line 6090, and can be displayed on a display 6081 serving as a display apparatus or stored in a recording apparatus such as an optical disk in a doctor room at another place or the like, so that a doctor at the remote place can perform diagnosis. It is also possible to record the information on a film 6110 serving as a recording medium by a film processor 6100 serving as a recording apparatus.

The present invention can provide a radiation imaging apparatus having an arrangement advantageous in reducing the influence of crosstalk on a signal from a radiation detection element.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation imaging apparatus, comprising:
   an imaging region including a plurality of detection elements each including a conversion element configured to convert radiation into an electric signal;
   a first signal line; and
   a signal processing circuit configured to process a signal output via the first signal line, wherein
   the plurality of detection elements include first and second detection elements that are connected to the first signal line,
   the first detection element having a first sensitivity to radiation that is different from a second sensitivity to radiation of the second detection element, and
   the signal processing circuit being configured to generate information related to irradiation of radiation to the imaging region by correcting a first signal obtained from the first detection element with a second signal obtained from the second detection element.

2. The radiation imaging apparatus according to claim 1, wherein the radiation imaging apparatus includes a scintillator configured to convert radiation into light, and
   the conversion element includes a photoelectric conversion element configured to convert the light into an electric signal.

3. The radiation imaging apparatus according to claim 2, wherein the second detection element includes a light shielding member arranged between the scintillator and the conversion element.

4. The radiation imaging apparatus according to claim 3, wherein the light shielding member comprises a bias line configured to apply a bias voltage to the conversion element, said bias line being arranged between the scintillator and the conversion element.

5. The radiation imaging apparatus according to claim 1, which is configured such that a first bias voltage applied to the conversion element included in the first detection element and a second bias voltage applied to the conversion element included in the second detection element are different from each other.

6. The radiation imaging apparatus according to claim 1, wherein the signal processing circuit is configured to generate the information related to radiation irradiation based on a difference between the first signal from the first detection element and the second signal from the second detection element.

7. The radiation imaging apparatus according to claim 1, wherein the information related to radiation irradiation includes at least one of a start of radiation irradiation, an end of radiation irradiation, a radiation irradiation intensity, and a radiation irradiation amount.

8. The radiation imaging apparatus according to claim 1, wherein the signal processing circuit is configured to output a signal for controlling a radiation source based on the information related to radiation irradiation.

9. The radiation imaging apparatus according to claim 1, further comprising a drive circuit configured to drive the plurality of detection elements; and
   a plurality of control lines configured to provide signals from the drive circuit to the plurality of detection elements for driving the plurality of detection elements, wherein
   the drive circuit periodically drives the first detection element and the second detection element.

10. The radiation imaging apparatus according to claim 9, wherein the plurality of control lines include a first control line and a second control line,
    the plurality of detection elements include third and fourth detection elements that are connected to a second signal line,
    the signal processing circuit is configured to process a signal output via the second signal line, and is configured to generate information related to radiation irradiation based on signals from the third and fourth detection elements, the first detection element and the third detection element are configured to be driven using the first control line, and the second detection element and the fourth detection element are configured to be driven using the second control line.

11. A radiation imaging system comprising:

the radiation imaging apparatus defined in claim 1; and a signal processing unit configured to process a signal from the radiation imaging apparatus.

* * * * *